US009717115B2

(12) United States Patent
Li et al.

(10) Patent No.: US 9,717,115 B2
(45) Date of Patent: Jul. 25, 2017

(54) TEXTILE OR NON-TEXTILE SHEET AND/OR FABRIC WITH ELECTRICAL FUNCTION

(71) Applicant: W.E.T. Automotive Systems AG, Odelzhausen (DE)

(72) Inventors: William Wei Li, Tianjin (CN); Sherry (Li) Chen, Langfang (CN); Stefan Huber, München (DE); Han-georg Rauh, Olching (DE)

(73) Assignee: GENTHERM GMBH, Odelzhausen (DE)

( * ) Notice: Subject to any disclaimer, the term of this patent is extended or adjusted under 35 U.S.C. 154(b) by 586 days.

(21) Appl. No.: 13/919,059

(22) Filed: Jun. 17, 2013

(65) Prior Publication Data

US 2013/0334202 A1 Dec. 19, 2013

(30) Foreign Application Priority Data

Jun. 18, 2012 (DE) .................... 10 2012 011 945
Apr. 15, 2013 (DE) .................... 10 2013 006 410

(51) Int. Cl.
*H05B 1/02* (2006.01)
*H05B 3/20* (2006.01)
(Continued)

(52) U.S. Cl.
CPC ............ *H05B 3/20* (2013.01); *A61F 7/007* (2013.01); *B60N 2/002* (2013.01); *B60N 2/5685* (2013.01); *B60N 3/044* (2013.01); *B60N 3/046* (2013.01); *H05B 3/03* (2013.01); *A61F 7/0097* (2013.01); *A61F 2007/0071* (2013.01); *A61F 2007/0077* (2013.01); *A61F 2007/0086* (2013.01)

(58) Field of Classification Search
CPC ...... A61F 2007/0071; A61F 2007/0077; A61F 2007/0086; A61F 7/007; A61F 7/0097; B60N 2/002; B60N 2/5685; B60N 3/044; B60N 3/046; H01H 31/023; H05B 3/03; H05B 3/20
USPC ................. 219/212, 494, 500, 541
See application file for complete search history.

(56) References Cited

U.S. PATENT DOCUMENTS 1,475,912 A   11/1923   Williams
2,978,972 A   4/1961    Hake
(Continued)

FOREIGN PATENT DOCUMENTS

DE   3513909        10/1986
DE   3938951 A1     5/1990
(Continued)

OTHER PUBLICATIONS

Automotive Heated Seats—Heated Steering Wheels, IGB Automotive Ltd., received by Assignee W.E.T. Automotive Systems, May 2003.
(Continued)

*Primary Examiner* — Dana Ross
*Assistant Examiner* — Joseph Iskra
(74) *Attorney, Agent, or Firm* — The Dobrusin Law Firm, P.C.

(57) ABSTRACT

The present invention relates to a flat-shaped article with an electrical function for placement in a functional tone. Provision is made that, even after having been placed, the flat-shaped article can again be removed without being destroyed from the functional zone.

18 Claims, 1 Drawing Sheet

(51) Int. Cl.
*A61F 7/00* (2006.01)
*H05B 3/03* (2006.01)
*B60N 2/56* (2006.01)
*B60N 3/04* (2006.01)
*B60N 2/00* (2006.01)

(56) References Cited

U.S. PATENT DOCUMENTS

| | | | |
|---|---|---|---|
| 3,034,140 A * | 5/1962 | Reynolds | A47K 3/002 4/583 |
| 3,287,684 A | 11/1966 | Armbruster, Jr. | |
| 3,448,246 A | 6/1969 | Armbruster | |
| 3,529,310 A | 9/1970 | Olmo | |
| 3,721,799 A | 3/1973 | Carlstrom | |
| 3,877,788 A | 4/1975 | Sprague et al. | |
| 3,892,946 A | 7/1975 | Rimmi | |
| 4,032,752 A | 6/1977 | Ohmura et al. | |
| 4,044,221 A | 8/1977 | Kuhn | |
| 4,149,066 A | 4/1979 | Niibe | |
| 4,245,149 A | 1/1981 | Fairlie | |
| 4,335,725 A | 6/1982 | Geldmacher | |
| 4,399,347 A | 8/1983 | Schmitt | |
| 4,410,790 A | 10/1983 | Berf et al. | |
| 4,436,986 A | 3/1984 | Carlson | |
| 4,523,085 A | 6/1985 | Grise | |
| 4,533,821 A | 8/1985 | Sato | |
| 4,539,051 A | 9/1985 | Hacias | |
| 4,542,285 A | 9/1985 | Grise | |
| 4,626,664 A | 12/1986 | Grise | |
| 4,628,187 A | 12/1986 | Sekiguchi et al. | |
| 4,633,068 A | 12/1986 | Grise | |
| 4,656,339 A | 4/1987 | Grise | |
| 4,661,689 A | 4/1987 | Harrison | |
| 4,665,304 A | 5/1987 | Spencer | |
| 4,713,531 A | 12/1987 | Fennekels et al. | |
| 4,719,335 A | 1/1988 | Batliwalla et al. | |
| 4,725,717 A | 2/1988 | Harrison | |
| 4,743,741 A | 5/1988 | Ramus | |
| 4,752,672 A | 6/1988 | Grise | |
| 4,761,541 A | 8/1988 | Batliwalla et al. | |
| 4,777,351 A | 10/1988 | Batliwalla et al. | |
| 4,845,343 A | 7/1989 | Aune et al. | |
| 4,849,255 A | 7/1989 | Grise et al. | |
| 4,857,711 A | 8/1989 | Watts | |
| 4,868,898 A | 9/1989 | Seto | |
| 4,888,089 A | 12/1989 | Marstiller et al. | |
| 4,892,988 A | 1/1990 | Marstiller et al. | |
| 4,912,306 A | 3/1990 | Grise et al. | |
| 4,923,248 A | 5/1990 | Feher | |
| 4,931,627 A | 6/1990 | Watts | |
| 4,964,674 A | 10/1990 | Altmann et al. | |
| 5,015,824 A | 5/1991 | Monter et al. | |
| 5,019,797 A | 5/1991 | Marstiller et al. | |
| 5,025,136 A | 6/1991 | Doege et al. | |
| 5,034,594 A | 7/1991 | Beezhold et al. | |
| 5,045,673 A | 9/1991 | Kelly | |
| 5,057,674 A | 10/1991 | Smith-Johannsen | |
| 5,081,339 A | 1/1992 | Stine | |
| 5,111,025 A | 5/1992 | Barma et al. | |
| 5,132,840 A | 7/1992 | Okada et al. | |
| 5,155,334 A | 10/1992 | Marstiller et al. | |
| 5,181,006 A | 1/1993 | Shafe et al. | |
| 5,187,350 A | 2/1993 | Tsuchiya | |
| 5,197,595 A | 3/1993 | Coultas | |
| 5,198,639 A | 3/1993 | Smuckler | |
| 5,206,482 A | 4/1993 | Smuckler | |
| 5,335,381 A | 8/1994 | Chang | |
| 5,344,591 A | 9/1994 | Smuckler | |
| 5,354,966 A | 10/1994 | Sperbeck | |
| 5,405,178 A | 4/1995 | Weingartner et al. | |
| 5,414,241 A | 5/1995 | Ohashi et al. | |
| 5,418,025 A | 5/1995 | Harmand et al. | |
| 5,422,462 A | 6/1995 | Kishimoto | |
| 5,432,322 A | 7/1995 | Ingram et al. | |
| 5,451,747 A | 9/1995 | Sullivan et al. | |
| 5,477,033 A | 12/1995 | Bergholtz | |
| 5,516,189 A | 5/1996 | Ligeras | |
| 5,543,601 A | 8/1996 | Bartrug et al. | |
| 5,626,021 A | 5/1997 | Karunasiri et al. | |
| 5,643,480 A | 7/1997 | Gustavsson et al. | |
| 5,679,277 A | 10/1997 | Niibe et al. | |
| 5,702,565 A | 12/1997 | Wu et al. | |
| 5,716,536 A | 2/1998 | Yokoto et al. | |
| 5,725,926 A * | 3/1998 | Wang | B60N 3/044 15/217 |
| 5,796,044 A | 8/1998 | Cobian et al. | |
| 5,800,483 A | 9/1998 | Vought | |
| 5,800,595 A | 9/1998 | Wright | |
| 5,801,914 A | 9/1998 | Thrash | |
| 5,824,993 A | 10/1998 | Chrysochoos et al. | |
| 5,824,994 A | 10/1998 | Noda et al. | |
| 5,824,996 A | 10/1998 | Kochman et al. | |
| 5,851,588 A | 12/1998 | Uthoff, Jr. | |
| 5,861,610 A | 1/1999 | Weiss | |
| 5,897,162 A | 4/1999 | Humes et al. | |
| 5,902,505 A | 5/1999 | Finley | |
| 5,904,874 A | 5/1999 | Winter | |
| 5,921,314 A | 7/1999 | Schuller et al. | |
| 5,948,297 A | 9/1999 | Haubner et al. | |
| 5,961,869 A | 10/1999 | Irgens | |
| 6,031,214 A | 2/2000 | Bost et al. | |
| 6,054,690 A | 4/2000 | Petit et al. | |
| 6,057,530 A | 5/2000 | Gurevich | |
| 6,064,037 A | 5/2000 | Weiss et al. | |
| 6,070,115 A | 5/2000 | Oestreicher et al. | |
| 6,084,217 A | 7/2000 | Bulgajewski | |
| 6,093,910 A | 7/2000 | McClintock et al. | |
| 6,097,009 A | 8/2000 | Cole | |
| 6,111,234 A | 8/2000 | Batliwalla et al. | |
| 6,124,577 A | 9/2000 | Fristedt | |
| 6,143,206 A | 11/2000 | Handa et al. | |
| 6,147,332 A | 11/2000 | Holmberg et al. | |
| 6,150,642 A | 11/2000 | Weiss et al. | |
| 6,164,719 A | 12/2000 | Rauh | |
| 6,172,344 B1 | 1/2001 | Gordon et al. | |
| 6,189,487 B1 | 2/2001 | Owen et al. | |
| 6,194,692 B1 | 2/2001 | Oberle | |
| 6,215,111 B1 | 4/2001 | Rock et al. | |
| 6,220,659 B1 | 4/2001 | McDowell et al. | |
| 6,229,123 B1 | 5/2001 | Kochman et al. | |
| 6,233,776 B1 * | 5/2001 | Blum | A47L 13/29 15/215 |
| 6,278,090 B1 | 8/2001 | Fristedt et al. | |
| 6,294,758 B1 | 9/2001 | Masao et al. | |
| 6,307,188 B1 | 10/2001 | Bulgajewski | |
| 6,369,369 B2 * | 4/2002 | Kochman | A41D 13/0051 219/528 |
| 6,403,935 B2 * | 6/2002 | Kochman | H02H 5/043 219/212 |
| 6,415,501 B1 * | 7/2002 | Schlesselman | H05B 3/283 219/528 |
| 6,426,485 B1 | 7/2002 | Bulgajewski et al. | |
| 6,439,658 B1 | 8/2002 | Ganz et al. | |
| 6,452,138 B1 | 9/2002 | Kochman et al. | |
| 6,455,823 B1 | 9/2002 | Bulgajewski et al. | |
| 6,495,809 B2 | 12/2002 | Bulgajewski et al. | |
| 6,501,055 B2 | 12/2002 | Rock et al. | |
| 6,512,203 B2 | 1/2003 | Jones et al. | |
| 6,559,422 B2 | 5/2003 | Burt | |
| RE38,128 E | 6/2003 | Gallup et al. | |
| 6,619,736 B2 | 9/2003 | Stowe et al. | |
| 6,629,724 B2 | 10/2003 | Ekern et al. | |
| 6,664,512 B2 | 12/2003 | Horey et al. | |
| 6,664,518 B2 | 12/2003 | Fristedt et al. | |
| 6,676,207 B2 | 1/2004 | Rauh et al. | |
| 6,686,562 B1 | 2/2004 | Weiss et al. | |
| 6,710,303 B1 | 3/2004 | Lorenzen | |
| 6,713,733 B2 | 3/2004 | Kochman et al. | |
| 6,838,647 B2 | 1/2005 | Nagele | |
| 6,840,576 B2 | 1/2005 | Ekern et al. | |
| 6,857,697 B2 | 2/2005 | Brennan et al. | |
| 6,869,139 B2 | 3/2005 | Brennan et al. | |
| 6,869,140 B2 | 3/2005 | White et al. | |
| 6,872,882 B2 | 3/2005 | Fritz | |

(56) References Cited

U.S. PATENT DOCUMENTS

| | | |
|---|---|---|
| 6,884,965 B2 | 4/2005 | Nelson et al. |
| 6,892,807 B2 | 5/2005 | Fristedt et al. |
| 6,893,086 B2 | 5/2005 | Bajic et al. |
| 6,906,293 B2 | 6/2005 | Schmiz et al. |
| 6,976,734 B2 | 12/2005 | Stoewe |
| 7,036,283 B2 | 5/2006 | Halas |
| 7,040,710 B2 | 5/2006 | White et al. |
| 7,052,091 B2 | 5/2006 | Bajic et al. |
| 7,053,344 B1 | 5/2006 | Surjan et al. |
| 7,083,227 B2 | 8/2006 | Brennan et al. |
| 7,100,978 B2 | 9/2006 | Ekern et al. |
| 7,131,689 B2 | 11/2006 | Brennan et al. |
| 7,147,279 B2 | 12/2006 | Bevan et al. |
| 7,168,758 B2 | 1/2007 | Bevan et al. |
| 7,202,444 B2 | 4/2007 | Bulgajewski |
| 7,205,510 B2 | 4/2007 | Howick |
| 7,213,876 B2 | 5/2007 | Stoewe |
| 7,223,948 B2 | 5/2007 | Howick et al. |
| 7,285,748 B2 | 10/2007 | Nelson et al. |
| 7,301,441 B2 | 11/2007 | Inada et al. |
| 7,306,283 B2 | 12/2007 | Howick et al. |
| 7,338,117 B2 | 3/2008 | Iqbal et al. |
| 7,356,912 B2 | 4/2008 | Iqbal et al. |
| 7,370,911 B2 | 5/2008 | Bajic et al. |
| 7,475,938 B2 | 1/2009 | Stoewe et al. |
| 7,478,869 B2 | 1/2009 | Lazanja et al. |
| 7,500,536 B2 | 3/2009 | Bulgajewski et al. |
| 7,506,938 B2 | 3/2009 | Brennan et al. |
| 7,510,239 B2 | 3/2009 | Stowe |
| 7,560,670 B2 | 7/2009 | Lorenzen et al. |
| 7,587,901 B2 | 9/2009 | Petrovski |
| 7,618,089 B2 | 11/2009 | Stoewe et al. |
| 7,637,569 B2 | 12/2009 | Krobok et al. |
| 7,741,582 B2 | 6/2010 | Howick et al. |
| 7,816,632 B2 * | 10/2010 | Bourke, III ............ A43B 7/025 219/635 |
| 8,008,606 B2 * | 8/2011 | Kaiserman ............... A43B 7/04 219/211 |
| 8,456,272 B2 | 6/2013 | Rauh et al. |
| 8,702,164 B2 * | 4/2014 | Lazanja ............... B60N 2/5685 219/202 |
| 2002/0117495 A1 | 8/2002 | Kochman et al. |
| 2004/0100131 A1 | 5/2004 | Howick et al. |
| 2004/0160110 A1 * | 8/2004 | Enomoto ............... B60N 2/002 297/452.5 |
| 2005/0242081 A1 | 11/2005 | Howick |
| 2006/0015801 A1 | 1/2006 | Suh et al. |
| 2006/0138810 A1 | 6/2006 | Knoll et al. |
| 2007/0176471 A1 | 8/2007 | Knoll |
| 2008/0142494 A1 * | 6/2008 | Blake ................... B60N 2/5685 219/217 |
| 2008/0296942 A1 * | 12/2008 | Schweiker ........... B60N 2/5685 297/217.3 |
| 2009/0218855 A1 | 9/2009 | Wolas |
| 2010/0035356 A1 | 2/2010 | Shalyt et al. |
| 2010/0038356 A1 | 2/2010 | Fukuda et al. |
| 2010/0038357 A1 | 2/2010 | Fukuda et al. |
| 2010/0219664 A1 | 9/2010 | Howick et al. |
| 2010/0326976 A1 | 12/2010 | Nakajima et al. |
| 2011/0147357 A1 | 6/2011 | Bokelmann et al. |

FOREIGN PATENT DOCUMENTS

| Country | Number | Date |
|---|---|---|
| EP | 0202896 A2 | 5/1986 |
| GB | 2010650 A | 6/1979 |
| JP | 57134655 A | 8/1982 |
| JP | 62109385 A | 7/1987 |
| JP | H06-132069 A | 5/1994 |
| JP | H6-333666 | 12/1994 |
| JP | 2000333781 A | 12/2000 |
| JP | 2001-93656 A | 4/2001 |
| JP | 2011102657 * | 5/2001 |
| JP | 2002-270350 A | 9/2002 |
| JP | 2004055219 A | 2/2004 |
| JP | 2006-054131 A | 2/2006 |
| JP | 2006-324182 A | 11/2006 |
| JP | 2007-052945 A | 3/2007 |
| JP | 2007-227830 A | 9/2007 |
| JP | 2008-238926 A | 10/2008 |
| WO | 94/09684 A1 | 5/1994 |
| WO | 02/06914 A1 | 1/2002 |
| WO | 03/101777 | 12/2003 |
| WO | 2010/065411 A1 | 6/2010 |

OTHER PUBLICATIONS

Automotive Seat Heating Systems, Bauerhin International, received by Assignee W.E.T. Automotive Systems, May 2002.

GMT 830 Heating & Ventilation System, IGB Automotive Ltd., received by Assignee W.E.T. Automotive Systems, Jun. 2003.

* cited by examiner

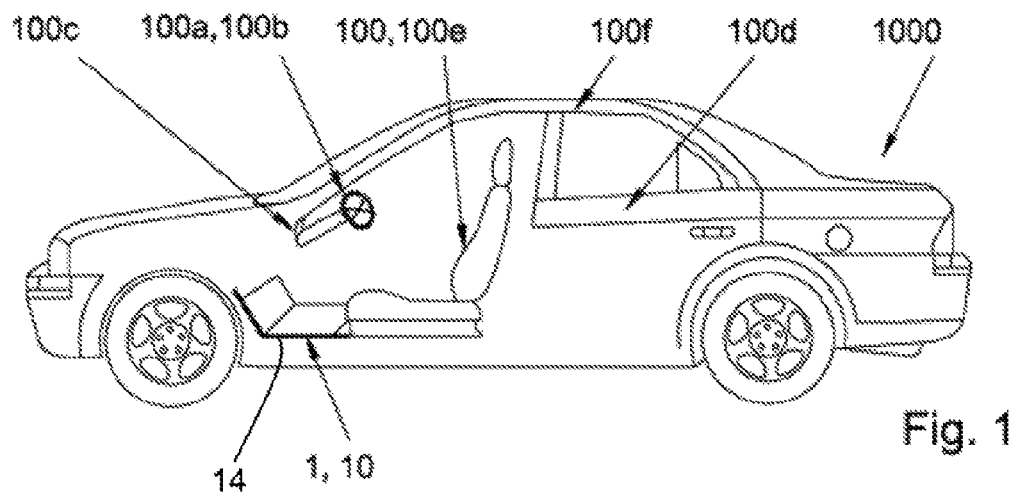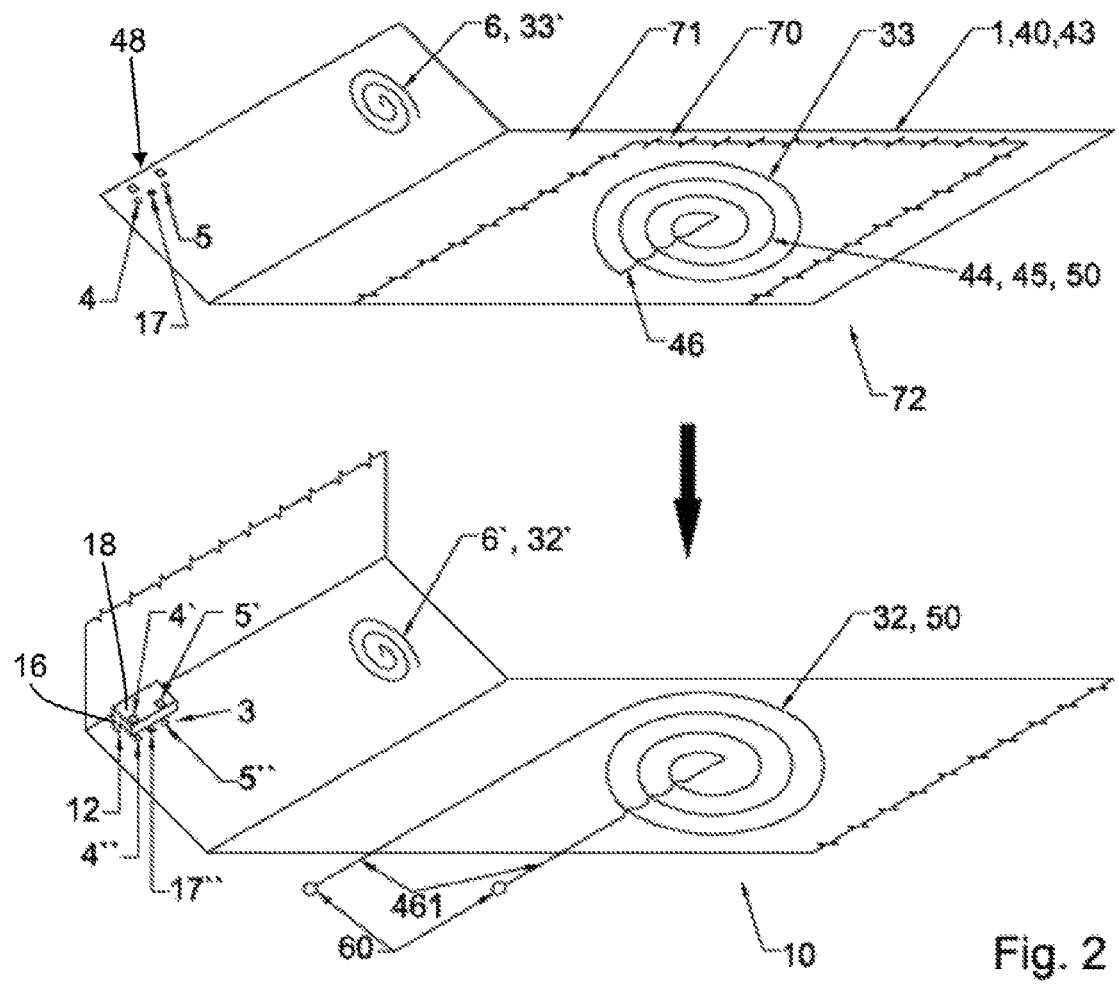

TEXTILE OR NON-TEXTILE SHEET AND/OR FABRIC WITH ELECTRICAL FUNCTION

OBJECT OF THE INVENTION

An object according to the present invention relates to a flat-shaped article 1 with an electrical function. The flat-shaped article can be a floor mat for a vehicle, a heating cover, especially for applying heat to unconscious patients, a heated carpet or to mat for detecting the presence of persons or animals.

Since it is desirable that generic flat-shaped articles at least temporarily be able to be removed from their place of use, they need a simple and safe connection with sufficient electrical conductivity. For it can be appropriate to remove a floor mat, for example for washing; to sterilize surgical materials in hospitals; or to move a carpet or covering on the floor as a user chooses. Until now, generic flat-shaped articles have perhaps been limited in offering these functions.

Therefore, in addition the invention relates to a device to electrically connect the flat-shaped article with a source of electrical energy.

FIGURES

In the following specification and the claims, particulars of the invention are explained. These explanations are for making the invention understandable. However, they are only examples. Naturally, within the framework of the invention defined by the independent claims, individual or multiple features can also be omitted, altered or supplemented. Also, the features of various embodiment forms can naturally be combined with each other. What is decisive is that the concept of the invention is implemented in essence. If a feature is to be implemented at least in part, then this also includes this feature being implemented completely or in essence completely. "In essence" especially means that the implementation permits attainment of the desired utility to a perceptible degree. This can especially mean that a corresponding feature is implemented at least 50%, 90%, 95% or 99%. If a minimum amount is indicated, then naturally more than this minimum amount can be used. If the number of a component is given as at least one, then this also includes embodiment forms with two, three or some other multiplicity of components. What is described for an object, can also be applied to the preponderant part or the totality of all other objects of the same type. If nothing eke is indicated, intervals include their limit points.

In what follows, reference is made to:

FIG. 1: Side view of a vehicle with an invention-specific flat-shaped article FIG. 2: Perspective view of a flat-shaped article from FIG. 2

SPECIFICATION OF THE INVENTION

The invention relates to the heating and/or monitoring of at least one object 100. Especially included in this are all objects or surfaces touched by persons or in danger of icing over, such as aircraft lifting surfaces, transmitters, refrigerators, interior furnishings of houses, doors, windows, roofs, couches, upholstery, etc. These can also for example be an interior furnishing item of an aircraft, ship, surface, railway or motor vehicle 1000 as per FIG. 1, such as a guidance device 100*a*, a steering wheel 100*b*, a dashboard 100*c*, an armrest, a door panel 100*d*, a seat, a vehicle headliner 100*f*, an item of upholstery, a cover 70, a seat 100*e* or, as here, a floor mat.

The present application claims priority to DE 102012011945.3 filed on Jun. 18, 2012 and DE 102013006410.4 filed on Apr. 15, 2013 both of which are incorporated by reference herein for all purposes.

The present teachings relate to a flat-shaped article comprising: an electrical function for placement in a functional zone, wherein the flat-shaped article even after its placement can again be removed from the functional zone without being destroyed.

The present teachings relate to a heated or monitored functional zone, wherein in a state in which a flat-shaped article with an electrical function is removed from its operating position, at least on its exterior surfaces, it is without electrical current.

At least one such object 100 possesses one or more functional zones 10. For example, these are surfaces to be heated or areas to be monitored of a passenger detection device.

To at least one object 100 to be heated and/or monitored and at least one functional zone 10, a flat-shaped article 1 is assigned with at least one electrical function. As in FIG. 1 or 2, this is a heated covering, a sensor-equipped floor mat, an air conditioner 40 or the like. The flat-shaped article 1 is situated at least partially in the functional zone 10. The functional zone 10 includes a floor 14 of the vehicle 1000.

Preferably at least one flat-shaped article exhibits at least one heating device 43 for heating the functional zone 10. Understood as a heating device 43 is any device that can be used to deliberately alter the temperature in its environment, for example all devices with at least one electrical resistance heater, a heat pump, a Peltier element and/or an air movement device such as a fan.

At least one heating device 43 preferably exhibits at least one electrical heating unit 44. Such a heating unit preferably is designed as a textile flat heating element. It can for example be used as an insert into the upholstery of an item of equipment such as a seat 100*e*.

At least one heating device 44 preferably exhibits one or more electrical resistance devices 45, to convert electrical energy into thermal. Preferably, one or in ore resistance devices 45 are configured so that at temperatures above 100° C., and also over 200° C. or over 250° C., depending on the instance of application, they at least partially lose their electrical conductivity. Depending on the instance of application, this can be under 150° C., under 200° C., or also under 260° C. At least one resistance device 45 and/or one of its component parts preferably exhibits a PTC effect.

At least one resistance device 45 preferably exhibits one or more cables 50 for heating.

Preferably at least one heating device 44 exhibits two or more electrodes 46, which are placed at intervals to each other at least partially on a resistance device 45. Preferably they are placed close to the edge along the resistance device 45 and attached on it, for example, by stitching, gluing, or pressing. They can exhibit a long extended contour, essentially meandering, and/or run in a straight line. Preferably they are situated roughly parallel to each other and are each connected at one of their ends via a connection line 461 with a source of current or voltage. If more than two contactor devices 48 are situated on a resistance device 45, then certain areas of them are able to be acted upon by current independent of the remaining ones.

In principle, electrodes 46 can be produced from the same materials as a resistance device 45. For that, preferably a larger amount of a conducting material is provided. This can for example be done in that a resistance device is silk-screen-printed for example on a flat carrier device. Then one or more layers are primed in the edge area, thus to form electrodes.

Such a flat-shaped article 1 can be of a module assembled from one or more layers. Preferably the flat-shaped article 1 contains protective layers to protect against major interference effects. Electrically conducting foils or textiles provide the necessary thermal energy.

Preferably such a flat-shaped article has at least one cover 70. What is meant by cover is any type of layer, cover underlayer or composite layer, which at least partially covers the flat-shaped article 1, especially such as is situated as a continuous flat component on flat-shaped article and/or in essence is able to be detached as a whole from it. Additionally or alternatively, a flat-shaped article 1 can also be provided with one or more coverings.

For some applications it can be appropriate if the flat-shaped article 1 on its underside 72 has as surface with high friction resistance, such as using a material with a high coefficient of friction like rubber. The same effect can also be attained by a high level of roughness, such as by use of coir fibers, ceramic granulates or roughened textiles.

For some applications, on its upper side 71 facing toward the user, the flat-shaped article 1 is equipped with a carpet, a textile, a polyurethane coating or something similar, to protect the flat-shaped article 1 against moisture and contamination, or to configure its surface to be pleasing to the touch.

Preferably the flat-shaped article 1 exhibits a sensor device to detect at least one ambient parameter. For an air conditioner 40, this for example can be a moisture sensor to determine the moisture in a seat and/or in the ambient air, or other parameters. In a heating device 44, it is for example temperature sensors which monitor the temperature level of the heating element and/or the environment, to ensure maximum comfort and safety. Such a temperature sensor can, for example, be a thermostat.

Provision can also be made that a sensor device detects a person or a passenger. It can, for example, react to a change in its electromagnetic field, the ambient pressure, an adjoining potential or its electrical capacitance. It can issue a signal about this event, or, for example, cause components to go into or out of operation. For example it could cause a heater or air conditioner, a radio, a belt monitor, an automatic pilot, a parking aid, or the like to work upon detecting a person, or shut the system in question off in his absence.

It is desirable that also after it has been installed, the flat-shaped article 1 can again be removed from the functional zone 10 without being destroyed. This requires electrical connections to be able to be simply detached and quickly attached again to an energy source 60.

Preferably the flat-shaped article exhibits at least one connection device 48, which works together with an appropriate attachment device 3 on the side of the energy source, to apply electrical current to the flat-shaped article 1. In relation to the floor 14 of the vehicle 1000 the attachment device 3 includes a generally vertical portion 16 and a generally horizontal portion 18 cantilevering from the vertical portion 16. The horizontal portion 18 is spaced apart from the floor 14 of the vehicle 1000.

Energy can be transmitted between the attachment device 3 and the connection device 48 by transmitting an electric current to electrically conducting contact surfaces 4, 5 on the connection device 48 that touch the corresponding contact surfaces 4', 5' on the attachment device 3.

It can be appropriate if the particular contact surfaces 4,5, in the installed state, are pressed against each other by contact pressure. This can for example be achieved by a mechanical spring, a magnet or a clamping lever.

Plug-type connectors are known to secure floor mats to one or more corners on the floor of a vehicle. Provision can be made that such a fixing device is also used as an attachment device 3.

To avoid contamination between the contact surfaces of the connecting device and attachment device 3, it can be advantageous to have the contact surfaces not be parallel to the functional zone 10.

Then rather it is more appropriate if the flat-shaped article 1 exhibits at least one connection device which is in electrically conducting contact with at least one attachment device 3 at least one contact surface, and if the contact surface is placed at a slant relative to the functional zone 10.

For this, preferably also at least a part of the flat-shaped article is inclined, so that the attaching device 3 can also be contacted, if it, for example, is placed in a wall or an inclined floor section. Preferably with a vehicle floor mat the attachment device 3 is provided in the walls, which are situated to the side of a passenger relative to the direction of travel. Another suitable position are slanted sections, which lie in front of the pedals relative to the travel of direction.

Preferably at least one contact surface carrying current assigned to functional zone 10 is so arranged that it points away from a user and toward functional zone 10. By this means, it is already covered by the flat-shaped article 1 itself.

If at least one flat-shaped article 1, on the side of it facing a user, exhibits at least one electrical contact surface 4, 5, the contact surfaces 4', 5' of the attachment device 3 can be located on the horizontal portion 18 and thus contact the flat-shaped article 1 from above. For this, a handle, an insertion rail or a leaf spring can be provided, below which the flat-shaped article 1 can be slid in at least at one edge section or a corner. In this case the flat-shaped article 1 carries contact surfaces 4, 5 of the connection device 48 on its upper side. By this means, these contact surfaces 4, 5 can be in electrical contact with the attachment device 3. Such leaf springs or rails are preferably situated along the front edge or a side edge of a floor mat.

One arrangement of contact surfaces 4, 4', 5, 5' in an edge zone that is not accessible to a user, or only with difficulty, is possible as an addition or alternative, for example in that one or more corners of a floor mat contact corners especially in areas lateral to and in front of the pedals relative to the direction of travel, and are secured.

A securing device 12 for securing the flat-shaped article which is arranged over at least one contact surface 4", 5", so that even if the flat-shaped article is in a dismantled condition, it covers at least one of the contact surface, can also prevent an unintended contact of electrical contact surfaces.

At least one functional zone 10 or an attachment device 3 assigned to it, preferably in a state in which a flat-shaped article 1 assigned to it with an electrical function or its connection device is removed from its operating position, exhibits no exterior surfaces carrying current. Thus, at least on its exterior surfaces, it is free of electrical current.

What is understood here especially by exterior surfaces are all areas which point from the functional zone 10 to a user, or which can easily be touched by persons during normal utilization of the heated or monitored object 100.

It can be ensured that such exterior surfaces are free of electric current, for example, in that to a functional zone 10 a covering device is assigned, which covers electrical contact surfaces when the flat-shaped article 1 is removed. It is appropriate, when the connection device is removed, that the covering device automatically is placed before the contact surfaces of the attachment device 3. This can, for example, occur with rotating disks that are only to be removed from the connection device. Another possibility is rubber-elastic covering devices which cover the current-carrying zones via beads or automatically self-closing openings.

Another possibility for implementing current-free exterior surfaces is to cut the current or apply current to contact surfaces by means of an appropriate switching device, thus shutting it on and off. For this, the connection device can operate a switch with inserted pins, magnets or other means, which interrupts the flow of current to at least one of the contact surfaces. In this way, even with systems with high operating voltage, the contact surfaces can stay uninsulated vis-à-vis the user. If inserted pins are used, then they are preferably configured so that an interruption is avoided; the openings on the attachment device 3 do not allow the usual foreign bodies like shoe heels, stones or keys to pass, and at the same time permit safe switching on and off of the current. Appropriate for this are flat, sawtooth-shaped curved straps or short elevations in the shape of the tip of a Phillips-bead screwdriver. These can be screened by additional annular straps to reduce the danger of injury.

Preferably the switching device is coupled with a closing mechanism, such as in the form of a key or a lock, for example with inserted pins in special shapes such as a cross slot. By this means, unintentional, flow of current is avoided if another object like the heel of a shoe or a user touches the contact surfaces 4,5.

However, preferably the closing mechanism and/or the operating current are magnetically switched. For this, preferably there is a switch in the attachment device 3, which interrupts current in its home position. If the switch comes under the influence of a magnetic field of a magnet situated on the connection device, then the switch closes, so that the connection device receives current.

For contacting, the attachment device means 3 also exhibit an RA1 resistance. This also only switches on when it is desired to have current flow to the flat-shaped article.

For avoiding electrical contacts and exterior surfaces carrying current, electrical energy can also be transferred without a direct electrical contact between the flat-shaped article and its functional elements on the one hand and the energy source on the other hand, for example by an inductive current transfer. For this, preferably to one functional zone 10 at least one energy emission device 32, 32' is assigned, to emit energy to the flat-shaped article 1 or to its electrical functional elements, for example in the form of an electrical emission coil 6'. This coil can, for example, exhibit a wire or a cord, which is wound about a spool axis or a pivot point, as a cylindrical wire roll, for example. However, it can also exhibit the form of a worm, the spool diameter of which can be altered, especially increasing from inside toward the outside. The spool can for example also be secured by a thread on a base or itself form a pan of a sewing thread or itself be a sewing thread. This kind of spool arrangement saves a great deal of space, especially on a carpet on the floor and/or a mat to be supplied.

Preferably the flat-shaped article 1 and/or its attachment device 3 exhibits at least one power-consumption device 33, 33', to do a contactless supply of energy to at least one electrical component of the flat-shaped article 1. Suitable for this, for example, is an electrical coil which permits energy into an electromagnetic field, between the connection device or the flat-shaped article 1 as a whole on the one hand and the attachment device 3 on the other hand.

The flat-shaped article 1 for its part or the connection device for its part exhibits an appropriate electrical coil 6, 6', to draw electrical energy out of the electromagnetic field. Provision can also be made that the induced field directly generates electric current in the electrical functional element of the flat-shaped article. In appropriate fashion, with such an arrangement a coil is formed from a heat conductor as a resistance device 45. In appropriate fashion, here the ends of the coil are connected with each other via an electrode 46. Preferably the resistance device 45 exhibits an insulated copper wire. Such a coil heat conductor system is preferably excited at a resonant frequency in the kilohertz range. By this means, the energy transfer efficiency is over 90%.

By this means, for example, a heating element can be used directly to generate heat through inductive action. However, a second coil can also be provided, which withdraws energy from the electromagnetic field and feeds it to the flat-shaped article 1 in functional elements, especially a thermal resistance device.

Preferably an electrical coil 6, 6' exhibits between 1 and 1000 windings, preferably between 10 and 100 windings. Preferably at least 50% of the basic surface of the flat-shaped article 1 is situated within one or more spirals. Preferably at least one spiral is provided, which exhibits at least one winding, which comprises at least 50% of the basic surface of the flat-shaped article 1, preferably at least 70%, better 90%. Such a design allows for efficient utilization of a magnetic field impressed from outside.

For guiding the flat-shaped article 1 with its contact device 48 or its energy consumption device 33 at its prescribed operating position in the functional zone 10 relative to attachment device 3, guidance devices 17, 17' can be used, for example in the form of insertable pins. Especially practical is the use of magnets, which, when the connection device is brought close to the attachment device 3, complete an exact automatic adjustment of the two components relative to each other. In addition, such magnets can also generate a contact pressure force between electrical contacts of the connection device and the attachment device 3, to cause a sufficient contact pressure between the two contacts. By this means, the transition resistance is kept low.

The air conditioning device 40 or one or more of its components (such as the resistance device 45, contacting device 48, . . . ) has one or more cables 50. These can be designed for example as electrodes 46, a contacting device or connecting cables 461 for providing current, as a resistance device 45 for heat generation and/or as sensor devices, for example as temperature or moisture sensors.

If the flat-shaped article 1 exhibits at least one carrier and at least one heating device 44, and if at least one of the heating devices 44 or at least one part of their thermal resistances is drawn away via at least one edge of the carrier and turned over onto the rear side of the carrier, thus bent around behind the carrier, then the carrier is able to be heated over its entire surface, but at least on the turnover edge to the margin. This is especially appropriate if a plurality of such carriers is placed next to each other, and a cold zone between two carriers is to be avoided.

Preferably the flat-shaped article 1 exhibits a flat carrier, for example made of toil or textile. Preferably at least one heat conductor is sewn onto the carrier. The carrier with the heat conductor preferably is embedded in latex, foam rubber, polyurethane foam or some other elastic material, to form as floor mat. It can be appropriate, before embedding into the elastic mass, to cover the carrier plus the heat conductor with a polyurethane foil on one or more sides, to avoid penetration of the elastic mass into the textile carrier. Preferably the carrier and/or a heat conductor situated thereon is embedded at least in sections within a floor mat along the plane of the mat so as to be able to slide relative to the surrounding elastic mass.

It can be appropriate if the flat-shaped article 1 or at least one of its component parts, like a carrier or a rubberizing layer, exhibits ferrite as a component part. Especially suitable are admixtures of ferrite in powder or granulated form. If ferrite is placed within the coil, this improves the efficiency of contactless energy transfer, since it guides the magnetic flux of an electromagnetic field through the coil.

LIST OF REFERENCE SYMBOLS

1 Flat-shaped article
3 Attachment device
4, 4', 4", 5', 5" contact surface
6, 6" coil
10 Functional zone
12 Securing device
17, 17' Guiding device
32, 32' Energy release device
33, 33' Energy consumption device
40 Air conditioning device
43 heating device
44 heating device
45 resistance device
46 electrode
48 contactor device
50 cables
60 energy source
70 cover
71 upper side
72 lower side
100 object
100a steering device
100b steering wheel
100c dashboard
100d door panel
100e seat
100f vehicle headliner
461 connection cable
1000 motor vehicle

The invention claimed is:
1. An assembly comprising:
i. a flat-shaped article comprising:
a. a heating device; and
b. electrical contact surfaces;
ii. an attachment device located in a functional zone, the attachment device comprising electrical contact surfaces for applying electrical current to the flat-shaped article, the attachment device also securing the flat-shaped article to the functional zone;
wherein the attachment device includes a generally vertical portion and a generally horizontal portion cantilevering from the vertical portion, the electrical contact surfaces of the attachment device are located on the horizontal portion,
wherein the flat-shaped article is configured to be placed in the functional zone by positioning the flat-shaped article such that the electrical contact surfaces of the flat-shaped article face away from the functional zone and towards a user, the flat-shaped article is configured to be placed below the horizontal portion of the attachment device such that the electrical contact surfaces of the attachment device contact the electrical contact surfaces of the flat-shaped article from above so that the electrical current from an energy source in the functional zone is supplied to the heating device on the flat-shaped article, and after placement of the flat-shaped article in the functional zone, the flat-shaped article is configured to be removed from the functional zone without destroying the flat-shaped article, and
wherein the electrical contact surfaces of the attachment device face towards the functional zone and away from the user so that the functional zone is free of any current carrying surfaces exposed to the user.

2. The assembly according to claim 1, wherein the flat-shaped article comprises a thermostat.

3. The assembly according to claim 2, wherein the assembly comprises guidance devices for positioning the flat-shaped article in the functional zone.

4. The assembly according to claim 1, wherein part of the flat-shaped article on which the electrical contact surfaces are located is situated at a slant relative to a remainder of the flat-shaped article, and the attachment device is situated on a portion of the functional zone that is slanted relative to a remainder of the functional zone.

5. The assembly according to claim 1, wherein the functional zone is located in a vehicle and the flat-shaped article is a floor mat.

6. The assembly according to claim 1, wherein the flat-shaped article comprises a sensor device to detect presence of the user.

7. The assembly according to claim 6, wherein upon the sensor device detecting the presence of the user, the heating device is turned ON, and upon the sensor device detecting an absence of the user the heating device is turned OFF.

8. The assembly according to claim 3, wherein the guidance devices comprise magnets.

9. The assembly according to claim 3, wherein the guidance devices comprise a magnet located between the electrical contact surfaces of the flat-shaped article, and a corresponding magnet located in the functional zone.

10. The assembly according to claim 1, wherein the heating device comprises at least one of: a heat pump, a Peltier element, and a fan.

11. The assembly according to claim 1, wherein the electrical contact surfaces of the flat-shaped article are located on a corner of the flat-shaped article.

12. An assembly comprising:
i. a floor mat comprising:
a. a heating device;
b. electrical contact surfaces;
c. a first guidance device that is a magnet located between the electrical contact surfaces of the floor mat;
ii. an attachment device located in a functional zone, the attachment device comprising:
a. electrical contact surfaces;
b. a second guidance device that is a magnet;
c. a generally vertical portion projecting from the functional zone; and
d. a generally horizontal portion that cantilevers from an upper portion of the vertical portion, the electrical contact surfaces of the attachment device are located on the horizontal portion;
wherein the functional zone includes a floor of a vehicle,
wherein the attachment device is adapted to secure the floor mat to the floor of the vehicle and also apply electrical energy from an energy source in the functional zone to the floor mat,
wherein when the floor mat is secured to the floor of the vehicle, the electrical contact surfaces of the floor mat face away from the floor of the vehicle and the electrical contact surfaces of the attachment device are spaced apart from the floor of the vehicle and face towards the floor, wherein the floor mat is configured to be slid below the horizontal portion of the attachment device so that the electrical contact surfaces of the attachment device contact the electrical contact surfaces of the floor mat from above, wherein the magnet of the first guidance device cooperates with the magnet of the second guidance device to adjust and position the floor mat in the functional zone when the floor mat is initially brought close to the functional zone, and wherein part of the floor mat on which the electrical contact surfaces are located is situated at a slant relative to a remainder of the floor mat, and part of the floor of the vehicle on which the attachment device is located is situated at a slant relative to a remainder of the floor.

13. The assembly according to claim 12, wherein the floor mat comprises a thermostat.

14. The assembly according to claim 12, wherein the heating device comprises at least one of a heat pump, a Peltier element, and a fan.

15. The assembly according to claim 12, wherein when the floor mat is placed in the functional zone, the electrical contact surfaces of the floor mat face a user, and the electrical contact surfaces of the attachment device face away from the user.

16. The assembly according to claim 12, wherein an underside of the floor mat comprises rubber.

17. The assembly according to claim 12, wherein the electrical contact surfaces of the attachment device and the electrical contact surfaces of the floor mat are pressed against each other by contact pressure, wherein the contact pressure is achieved by a mechanical spring, a magnet, or a clamping lever.

18. The assembly according to claim 12, wherein the electrical contact surfaces of the attachment device that are located on the horizontal portion face towards the floor of the vehicle and away from a user in the functional zone.

* * * * *